(12) United States Patent
Loddenkemper et al.

(10) Patent No.: US 12,150,771 B2
(45) Date of Patent: Nov. 26, 2024

(54) SEIZURE DETECTION USING MULTIPLE BIOMEDICAL SIGNALS

(71) Applicants: CHILDREN'S MEDICAL CENTER CORPORATION, Boston, MA (US); WENTWORTH INSTITUTE OF TECHNOLOGY, Boston, MA (US)

(72) Inventors: Tobias Loddenkemper, Boston, MA (US); Hamed Salehizadeh, Boston, MA (US)

(73) Assignees: Children's Medical Center Corporation, Boston, MA (US); Wentworth Institute of Technology, Boston, MA (US)

( * ) Notice: Subject to any disclaimer, the term of this patent is extended or adjusted under 35 U.S.C. 154(b) by 938 days.

(21) Appl. No.: 17/083,114

(22) Filed: Oct. 28, 2020

(65) Prior Publication Data

US 2021/0038143 A1 Feb. 11, 2021

Related U.S. Application Data

(63) Continuation of application No. PCT/US2019/029575, filed on Apr. 29, 2019.
(Continued)

(51) Int. Cl.
*A61B 5/00* (2006.01)
*A61B 5/024* (2006.01)
(Continued)

(52) U.S. Cl.
CPC ........ *A61B 5/4094* (2013.01); *A61B 5/02405* (2013.01); *A61B 5/02416* (2013.01);
(Continued)

(58) Field of Classification Search
CPC .............. A61B 5/4094; A61B 5/02405; A61B 5/02416; A61B 5/0531; A61B 5/11; A61B 5/1101; A61B 5/7275; A61B 5/7282
See application file for complete search history.

(56) References Cited

U.S. PATENT DOCUMENTS 6,304,775 B1   10/2001  Iasemidis et al.
8,795,173 B2 *  8/2014  Poh ...................... A61B 5/7275
                                                              600/301

(Continued)

FOREIGN PATENT DOCUMENTS

CA        2958492 A1    3/2016
WO     2017007808 A1    1/2017

OTHER PUBLICATIONS

International Search report and Written Opinion for corresponding PCT Patent Application No. PCT/US19/29575, dated Jul. 3, 2019 (7 pages).

*Primary Examiner* — Devin B Henson
(74) *Attorney, Agent, or Firm* — Greenberg Traurig LLP; Melissa Hunter-Ensor; Kristopher Reichlen

(57) ABSTRACT

A method of detecting the likelihood of a seizure event in a patient includes at successive expirations of a first time interval, determining a first likelihood that the patient is experiencing a seizure based on electrodermal activity and a movement of a limb of the patient. The method also includes at successive expirations of a second time interval, determining whether the patient experienced a seizure in a second time period preceding the determining based on a heart rate of the patient. In response to determining that the third comparison result satisfies at least a third detection criterion, the method compares electrodermal activity and the movement of a limb of the patient to determine a second likelihood. In response to determining that the second likelihood
(Continued)

satisfies a second detection criterion, the method triggers presentation of a second alert regarding a potential seizure.

20 Claims, 9 Drawing Sheets

Related U.S. Application Data

(60) Provisional application No. 62/664,579, filed on Apr. 30, 2018.

(51) Int. Cl.
*A61B 5/0531* (2021.01)
*A61B 5/11* (2006.01)

(52) U.S. Cl.
CPC .............. *A61B 5/0531* (2013.01); *A61B 5/11* (2013.01); *A61B 5/7275* (2013.01)

(56) References Cited

U.S. PATENT DOCUMENTS

| | | | | |
|---|---|---|---|---|
| 8,805,484 B2 * | 8/2014 | Syed | ...................... | A61B 5/352 600/509 |
| 9,339,195 B2 * | 5/2016 | Pitruzzello | ............. | A61B 5/389 |
| 9,681,836 B2 * | 6/2017 | Sabesan | ............... | A61B 5/4094 |
| 2012/0271182 A1 * | 10/2012 | Liao | ...................... | A61B 5/024 600/508 |

* cited by examiner

Accelerometer Combined Feature (20 min before and after seizure)

PPG Feature (20 min before and after seizure)

SEIZURE DETECTION USING MULTIPLE BIOMEDICAL SIGNALS

CROSS-REFERENCE TO RELATED APPLICATION

This application is a U.S. National Stage filed under 35 U.S.C. § 111(a), which is a continuation of and claims priority to PCT/US2019/029575, filed Apr. 29, 2019, which claims the benefit of and priority to U.S. Provisional Application No. 62/664,579, filed Apr. 30, 2018, the entire contents of each of which are incorporated herein by reference in its entirety.

BACKGROUND

Epilepsy affects approximately 0.5% to 0.8% of the world population. Epilepsy often leads to a poor quality of life for patients due to injuries resulting from seizures, which in extreme cases include sudden unexpected death in epilepsy (SUDEP). Reliable seizure detection could reduce the risk of injuries to a patient, improve treatment and possibly prevent SUDEP.

Existing methods to predict seizures focus principally on analysis of brain electrical activity by electroencephalogram (EEG) or invasive monitoring.

SUMMARY

According to one aspect of the present application, a method is provided. The method may include, at successive expirations of a first time interval, determining whether a patient is experiencing a seizure. The determining whether the patient is experiencing the seizure may include: comparing first information regarding an electrodermal activity of the patient to at least one first condition to generate a first comparison result; comparing second information on a movement of a limb of the patient to at least one second condition to generate a second comparison result; generating a first likelihood based at least in part on the first comparison result and the second comparison result; and in response to determining that the first likelihood satisfies at least a first detection criterion, triggering presentation of a first alert regarding a potential seizure. The method may also include, at successive expirations of a second time interval longer than the first time interval, determining whether the patient experienced a seizure in a second time period preceding the determining. The determining whether the patient experienced a seizure including: comparing third information on a heart rate of the patient to at least one third condition to generate a third comparison result; in response to determining that the third comparison result satisfies at least a third detection criterion: comparing fourth information on the electrodermal activity of the patient to the at least one first condition to generate the fourth comparison result; comparing fifth information on the movement of the limb of the patient to the at least one second condition to generate the fifth comparison result; generating a second likelihood based at least in part on the fourth comparison result and the fifth comparison result; and, in response to determining that the second likelihood satisfies at least a second detection criterion, triggering presentation of a second alert regarding a potential seizure.

According to another aspect of the present application, a device is provided. The device may include at least one processor and at least one storage having encoded thereon executable instructions that, when executed by the at least one processor, cause the at least one processor to perform the above method.

According to another aspect of the present application, at least one non-transitory storage medium is provided. The at least one non-transitory storage medium may be encoded with executable instructions that, when executed by at least one processor, cause the at least one processor to carry out the above method.

The foregoing summary is to be considered non-limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
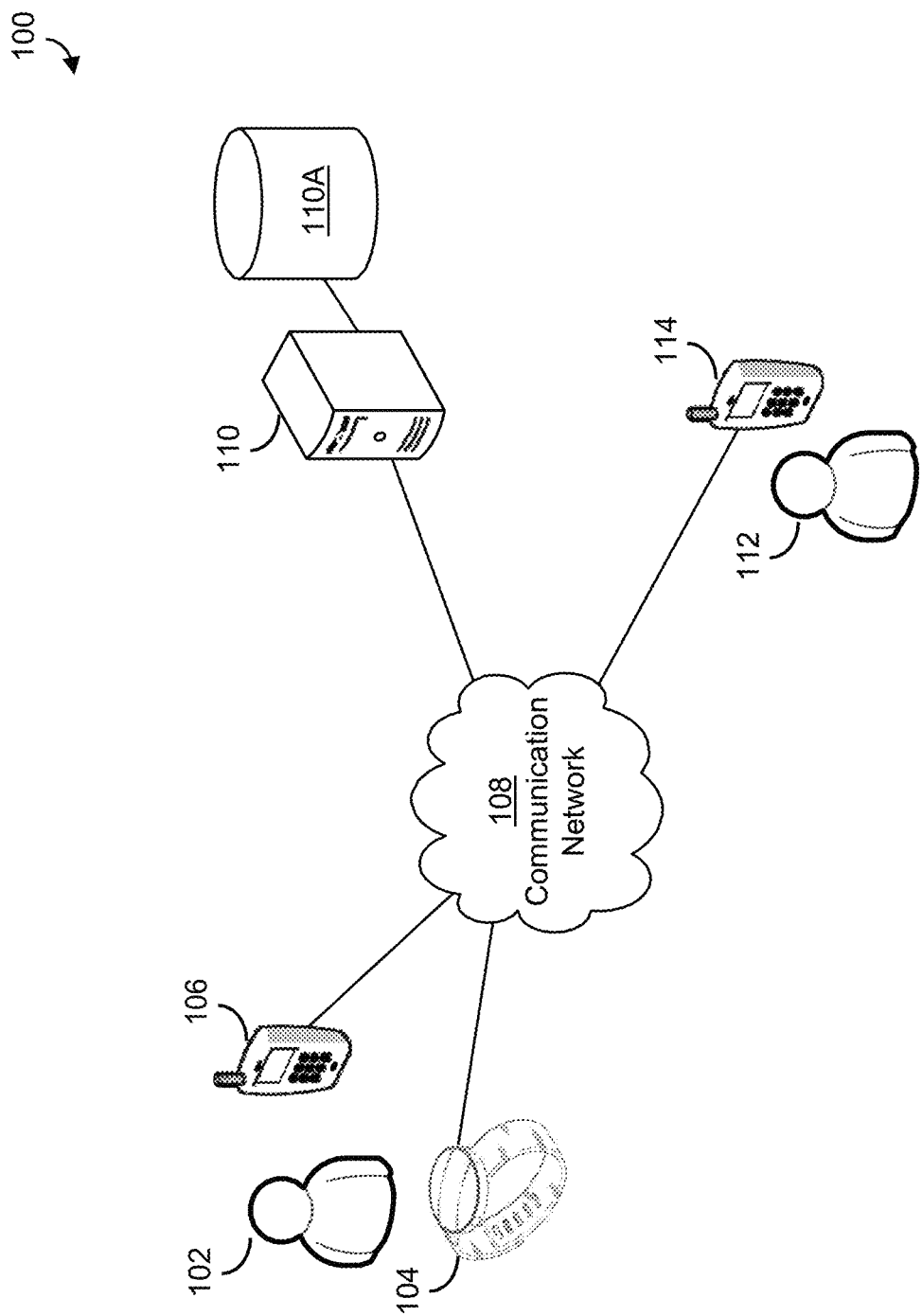
FIG. 1 is a diagram of illustrative components of a system with which some embodiments may operate.

Described herein are embodiments of a method and a device used to detect the occurrence of seizures for a patient (e.g., a human or animal) based on biomedical signals indicating physiological information of the patient. Such a device may, for example, be able to detect the probability that a seizure is presently occurring and/or will occur up to ten minutes in advance of a seizure and/or reliably detect whether a seizure has occurred in the recent past. For example, a seizure may be predicted with some probability up to one minute, up to two minutes, up to five minutes, or up to ten minutes in advance of a seizure. In response to an indication that it is highly probable (e.g., above a threshold) that a seizure will occur, or that a seizure has occurred, the device may notify a caretaker or some other user, such as the patient himself. The notification allows the caretaker and/or patient to prepare for the seizure or respond to the seizure by ensuring the safety of the patient.

The inventors have recognized and appreciated that patients would benefit greatly from a reliable way of determining the probability that a seizure is likely to occur or did occur in a particular time interval. Due to the danger inherent in epilepsy, it would be helpful to patients and caregivers to be able to determine the likelihood of the occurrence of a seizure, at any particular time. When the probability exceeds a threshold prior to the onset of the seizure itself, the epileptic patient or a caregiver can plan for the seizure, allowing the patient time to place themselves in a safe environment in which a seizure will not injure others or themselves (e.g., driving a car) or through the caregiver keeping a closer watch on the patient.

The inventors have recognized and appreciated that there are various disadvantages to existing techniques for seizure detection and prediction. Existing techniques focus on predicting seizures using electroencephalograms (EEGs) or more invasive monitoring of the brain. EEGs require a great deal of data regarding electrical activity within a patient's brain and require the placement of many sensors around the patient's skull and often the application of a conductive gel. Such a procedure is difficult to perform over a long term. The EEG is not designed to be freely mobile, to be used as patients go about their lives, and many patients may feel uncomfortable wearing an EEG monitor for an extended period of time. Moreover, many EEG techniques are only able to generate a reliable prediction of a seizure that applies to a few seconds or minutes following the prediction. The inventors have therefore recognized and appreciated that it would be advantageous to patients to have a device that is non-intrusive and may be used or worn as the patients move through a normal daily routine, and the advantages of a device that generates a reliable prediction of whether a patient will experience a seizure over the course of minutes following generation of the prediction.

The inventors have further recognized and appreciated that particular combinations of biomedical signals may be used to determine the probability that a seizure is occurring, will occur, or has already occurred. For example, features extracted from a photoplethysmogram (PPG) signal, an electrodermal activity (EDA) signal and an accelerometer (ACC) signal may be combined to detect or predict onset of a seizure in a time period (e.g., several minutes) following the detection/prediction and/or to detect whether a seizure has occurred in a time period preceding the detection. Both time-domain and frequency-domain features may be combined to determine a probability of seizure onset or detect whether a seizure occurred.

Conventionally, PPG has not been used as a signal in evaluating whether a seizure is occurring, has occurred, or will occur. This is because reliable monitoring of heart rate is difficult, as heart rate is heavily dependent on movement and changes in heart rate may be masked by movements of a patient, particularly movements related to an ongoing seizure. The inventors recognized and appreciated, however, that a PPG signal may be a viable indicator of whether a seizure is or has recently occurred, if the impact of movement can be mitigated or eliminated.

The inventors have additionally recognized and appreciated that while a change in heart rate may be masked by movements during a seizure episode, a seizure may have an impact on heart rate that may be relatively long lasting, such as lasting more than five minutes, more than seven minutes, or more than 10 minutes after the end of a seizure episode. As such, a PPG signal that exhibits characteristics similar to a post-seizure heart rate may be a useful tool to detect or confirm whether a seizure occurred in the recent past, even if the PPG signal could not itself be reliably used (due to movements) in all situations to detect whether a seizure is in progress at the time the PPG signal is collected.

The inventors have recognized and appreciated the advantages that would be offered by a seizure monitoring and detection scheme that incorporated PPG signal as a factor, but leveraged the PPG signal in a manner that accounted for its usefulness in confirming that a patient experienced a seizure in the recent past. For example, it may be advantageous in some embodiments to use some biomedical signals, such as EDA and accelerometer signals indicative of movement, to determine whether a seizure is in progress or will occur soon, but may not use PPG signals because of the risk that such PPG signals will be unreliable due to movements that often accompany a general tonic-clonic seizure. However, because EDA and movement may not be as accurate or as overall reliable as PPG signals in detecting a seizure, there may be advantages to using PPG signals in a different manner in a seizure detection process, one that may account for the difficulties posed by movement to a PPG signal. For example, while EDA and movement may be used to determine whether a seizure is in progress or will occur soon, PPG may be used to determine whether a seizure occurred in the recent past and is no longer ongoing.

Accordingly, examples are described below of techniques for generating a likelihood of seizure onset and of devices for use with such techniques. In some embodiments a method includes determining a likelihood of a patient experiencing a seizure within a first time period. This determining may be done at successive expirations of a first time interval. In some embodiments, the method further includes determining whether the patient experienced a seizure in a second time period, in the recent past. This determining may be done at successive expirations of a second time interval that is longer than the first time interval, and may be a time longer than many seizures last. The first time interval may be selected to be short enough to fit wholly within the duration of a seizure in progress (for a seizure of a common length, such as of an average length). The second interval, in contrast, may be selected to be long enough such that a seizure (of common length, such as of average length) may begin and end within the second interval. With intervals of these length, the first interval may be used in connection with monitoring for seizures in progress, while the second interval may be used in connection with monitoring for seizures that a patient experienced in the recent past.

In some embodiments, the first determination is based on a same set of features than the second determination. In other embodiments, the second determination may be based on a second set of features than the first determination. For example, the first and/or second determinations may be based on EDA information, PPG information, and information on a movement of the patient. However, as discussed above, it may be advantageous in some embodiments for the first determination to be based on EDA information and/or movement information, and not PPG information, while it may be advantageous for the second determination to be based on EDA information, movement information, and/or PPG information.

In some embodiments, a first likelihood is generated—at the first, shorter time interval—based on a comparison of EDA information of a patient to a first condition and a comparison of information on a movement of a limb of a patient to a second condition. If the first likelihood satisfies a first detection criterion, presentation of a first alert regarding a potential seizure is triggered. Heart rate information, such as PPG information, may not be used in connection with this shorter time interval, in some embodiments. In some embodiments, heart rate information of a patient is compared to a third condition to determine whether to calculate a second likelihood. If the heart rate information is indicative of a seizure, the second likelihood is generated based on a comparison of EDA information of a patient to a first condition and a comparison of information on a movement of a limb of a patient to a second condition. If the likelihood satisfies a second detection criterion, presentation of a second alert regarding a potential seizure is triggered. In some embodiments, the alerts may include presenting the associated likelihood to the user, which may be a patient or a caregiver.

Various illustrative examples of techniques for seizure detection, and devices for combining features of multiple biomedical signals of a patient and generating a likelihood of onset of a seizure, are described below. It should be appreciated, however, that embodiments are not limited to operating in accordance with any of the examples below, and that other embodiments are possible.

FIG. 1 illustrates an example of a system with which some embodiments may operate. In the system 100 of FIG. 1, a patient 102 operates a wearable device 104 and a computing device 106. The wearable device 104 is illustrated in FIG. 1 as a wristlet that is shaped and arranged to be worn on and attached to a wrist of the patient 102. It should be appreciated, however, that embodiments are not limited to operating with a wearable device that is arranged to be worn at any particular location on the body and embodiments may instead operate with a wearable device that may be worn at any suitable location on the body. For example, the wearable device 104 may be worn on a portion of an arm (e.g., a shoulder, an upper arm (bicep), a forearm, or a wrist), a portion of a leg (e.g., a thigh, a calf, or an ankle), an ear, a forehead, a neck, a chest, a toe, a foot, a hand, or a finger of the patient.

The wearable device 104 may include one or more sensors to collect information that may be analyzed to generate a likelihood that the patient 102 will experience a seizure. For example, in some embodiments the wearable device 104 may include a PPG sensor (e.g., a pulse oximeter), an EDA sensor and an accelerometer. In some embodiments, the wearable device may additionally include a thermometer, an electrocardiograph, and/or one or more sensors to detect a body temperature of the patient 102. The wearable device 104 may include a storage device to store data collected by the sensor(s).

In some embodiments, the wearable device 104 may include one or more processors or other control circuits configured or programmed to analyze the data generated by the one or more sensors and to generate a likelihood that the patient is experiencing a seizure. For example, the wearable device 104 may store and execute a seizure detection facility to generate the likelihoods and any associated alerts. Upon generating the likelihood, the wearable device 104 may output an alert via a user interface of the device 104, such as via a display screen, a light (e.g., a light-emitting diode (LED)), a speaker, a vibration circuit, and/or other form of output. In some embodiments, the wearable device 104 may additionally or alternatively transmit the likelihood, together with any other suitable information, to the computing device 106 for output, such as via wired and/or wireless transmission components of the wearable device 104. The likelihood may be communicated to the device 106 in any suitable manner, including as a voice message, a text message (e.g., SMS message), an email, or other message. For example, the computing device 106 may be implemented as a mobile device such as a smartphone, and the device 104 may transmit the likelihood to the mobile device, such as to an "app" implemented on the smart phone, to present the likelihood and/or an alert to the patient 102. The computing device 106 is illustrated in FIG. 1 as a smartphone, but it should be appreciated that in embodiments other forms of computing devices may be used, such as laptop or desktop personal computers, personal digital assistants (PDAs), or other devices. In such embodiments, the wearable device 104 may transmit the data via a communication network 108, discussed below.

In some embodiments, the wearable device 104 (and/or the device 106) may also transmit the data from the one or more sensors to one or more servers 110. The device 104 may transmit the information to the server(s) 110 over the communication network 108. The server(s) 110 may be implemented as any suitable computing device or array of computing devices, as embodiments are not limited in this respect. For example, the server(s) 110 may be a distributed network of servers, a desktop or laptop personal computer, a mobile device, or other computing device to analyze data. In some embodiments, the server(s) 110 may be implemented as a mobile device operated by the patient 102, and may be the same device as the device 106. In other embodiments, the server(s) 110 may be operated by a medical care provider, such as a doctor's office, or by a provider of a seizure detection service, and may be located remote from the patient 102.

Server(s) 110 may be configured to store the received information in a data store 110A. Information may be stored in the data store 110A in association with an account for the patient 102 or otherwise in association with information identifying the patient 102 to indicate that the information relates to patient 102. In some embodiments, the server(s) 110 may additionally relay information, including the likelihood, to other devices that have been associated (e.g., through prior configuration input) in the data store 110A with the patient 102. For example, the data store 110A may store information indicating that the patient 102 is associated with the device 104, the device 106, and/or the device 114 (e.g., via an association between the patient 102 and the caregiver 112). In response to identifying that association, the server(s) 110 may relay information to one or more of those devices. In some embodiments, the wearable device 104 (and/or device 106) may not be configured to analyze data to generate a likelihood that the patient 102 is experiencing and/or recently experienced a seizure. Instead, in some such embodiments, the server(s) 110 may include one or more processors or other control circuits to analyze the data and generate the likelihood. For example, the server(s) 110 may store and execute a seizure detection facility to generate the likelihood. In such embodiments, the server(s) 110 may store the likelihood in the data store 110A and may transmit the likelihood to the wearable device 104 and/or the device 106 for output to the patient 102. In such embodiments, the server(s) 110 may transmit the likelihood via the communication network 108.

In some embodiments in which the server 110 is separate from the device 106, instead of or in addition to a server 110 receiving the sensor data from the wearable device 104, storing the sensor data, executing a seizure detection facility to analyze the data to generate a likelihood, and transmitting the likelihood to the wearable device 106 for output, the device 106 may be configured to perform one or more of these functions, including by storing and executing the seizure detection facility and/or by relaying communications (including data and/or likelihoods) between the device 104 and server 110.

In some embodiments, the wearable device 104, the device 106, and/or the server(s) 110 may additionally communicate to a caregiver 112 the likelihood the patient 102 is experiencing or recently experienced a seizure. Caregiver 112 may be a person who may care for the patient 102, such as a friend or family member of patient 102 or a medical professional such as a doctor or nurse. In some such embodiments, the device 104, device 106, and/or server(s) 110 may transmit the likelihood, via the communication network 108, to a device 114 operated by the caregiver 112. The device 114 may be any suitable computing device, as embodiments are not limited in this respect. The likelihood may be communicated to the device 114 in any suitable manner, including as a voice message, a text message (e.g., SMS message), an email, or other message. For example, the computing device 114 may be implemented as a mobile device such as a smartphone, and the device 104 may transmit the likelihood to the mobile device, such as to an "app" implemented on the smart phone, to present the likelihood and/or an alert to the caregiver 112. The computing device 114 is illustrated in FIG. 1 as a smartphone, but it should be appreciated that in embodiments other forms of computing device may be used, such as laptop or desktop personal computers, personal digital assistants (PDAs), or other devices.

The communication network 108 by which the devices of system 110 may communicate may be or include one or more wired and/or wireless networks. In some embodiments, the network 108 may include one or more wireless personal area networks (WPAN), one or more wireless and/or wired local area networks (LANs), and/or one or more wireless and/or wired wide area networks (WANs), and in some embodiments may include the Internet.

As discussed above, in some embodiments a device (e.g., wearable device 104 and/or server(s) 110) may execute a seizure detection facility that analyzes biological information for a patient and generates a likelihood that the patient is experiencing a seizure. FIGS. 2-5 illustrate examples of methods/processes that may be implemented by a device according to some embodiments.

Figure 2:
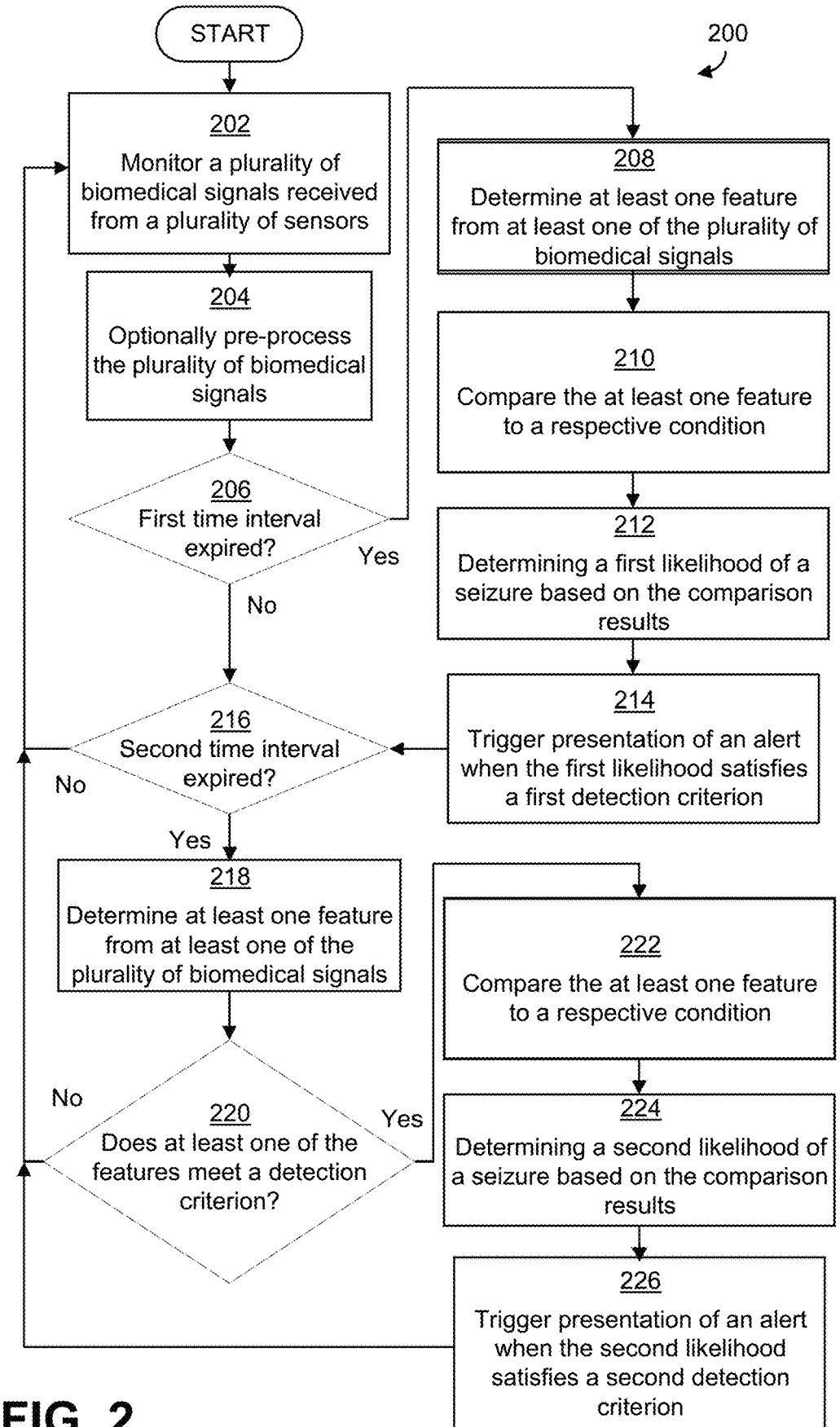
FIG. 2 is a flowchart of an example method that some embodiments may implement to detect a seizure.

Referring to FIG. 2, a method 200 of predicting seizures in a patient includes multiple blocks. In some embodiments, certain blocks shown in FIG. 2 may not be performed. For example, the pre-processing of act 204 may not be performed in some embodiments. In some embodiments, additional blocks that are not shown in FIG. 2 may be included in the method 200. Additionally, the order of the blocks in method 200 is not limiting. Some embodiments may perform the blocks of method 200 in a different order than that shown in FIG. 2. For example, multiple blocks may be performed simultaneously.

The process 200 begins in block 202, in which the seizure detection facility monitors a plurality of biomedical signals received from a plurality of sensors. By way of example and not limitation, the plurality of sensors may include a EDA sensor, a heart rate sensor (e.g., a PPG sensor), and a motion sensor (e.g., an accelerometer). In some embodiments, the patient wears a wearable device incorporating the sensors and the seizure detection facility. The biomedical signals may take the form of data transmitted by the sensor(s) in any form. The signal may be an analog signal or a digital signal. For example, the data generated by the sensors may include values for biological characteristics that the sensors generated continuously and/or at discrete sampling intervals (e.g., multiple times a second, every minute, every few minutes, several times an hour, or any other suitable interval) and each value may be associated with a time the value was generated. The time may be an absolute time, such as a time of day and/or date, or may be an elapsed time from a reference point such as a start of monitoring, or may be any other suitable time.

In some embodiments, the EDA data is received from the EDA sensor every 1 minute with a 10 second overlap with the previous window of data, the accelerometer data is received from the accelerometer every 12 seconds with a 6 second overlap with the previous window of data, and the PPG data is received every 12 seconds with a 6 second overlap with the previous window of data. Though, it should be appreciated that other embodiments may include other windows for collection and transmission of sensor data.

In block 204, the sensors and/or the seizure detection facility pre-process the biomedical signals. Pre-processing may occur to the signals from the sensors while the biomedical signals are in analog form, after conversion to a digital format, or both. By pre-processing the biomedical signals, unwanted data may be removed from the biomedical signals, thereby increasing the accuracy of the seizure prediction.

In some embodiments, EDA signals may be preprocessed by applying a low pass filter. The low pass filter may have, for example, a cut-off frequency of 2 mHz. Alternatively or additionally, the EDA signals may be preprocessed by applying a smoothing filter. For example, a Hodrick-Prescott filter may be used to smooth the EDA signals. In some embodiments, accelerometer signals may be preprocessed by applying a bandpass filter. The bandpass filter may have, for example, cut-off frequencies of 0.5 Hz and 30 Hz.

In some embodiments, PPG signals may be preprocessed by downsampling the PPG signals to half the original sampling rate. Alternatively or additionally, the PPG signals may be preprocessed by applying a bandpass filter. The bandpass filter may filter out DC components and high frequency components of the PPG signals. In some embodiments, the bandpass filter may pass frequencies that range from 0.1 to 20 Hz, 0.1 to 10 Hz, 0.1 to 8 Hz, or 0.1 to 5 Hz. In some embodiments, a Butterworth filter is also used to maintain a flat frequency response.

It should be understood that additional preprocessing may be performed. Moreover, since the pre-processing may be optional, subsequent blocks of method 200 may apply to the original biomedical signals or preprocessed versions of the biomedical signals.

Referring back to FIG. 2, in block 206 the seizure detection facility determines whether a first time interval has expired. In some embodiments, the first time interval may be 30 seconds, 45 seconds, 60 seconds, 90 seconds or 120 seconds. If the first time interval has not expired, the method 200 continues to block 216. When the first time interval is determined to expire, the method 200 continues to block 208.

In block 208, the seizure detection facility determines at least one feature from at least one of the plurality of biomedical signals. The features may be referred to simply as information. In some embodiments, multiple features may be calculated from a single signal. The multiple features may be combined into a single "combined feature" associated with the associated biomedical signal. Examples of determining at least one feature based on EDA signals, accelerometer signals and PPG signals are shown in FIG. 3, FIG. 4, and FIG. 5, respectively.

Figure 3:
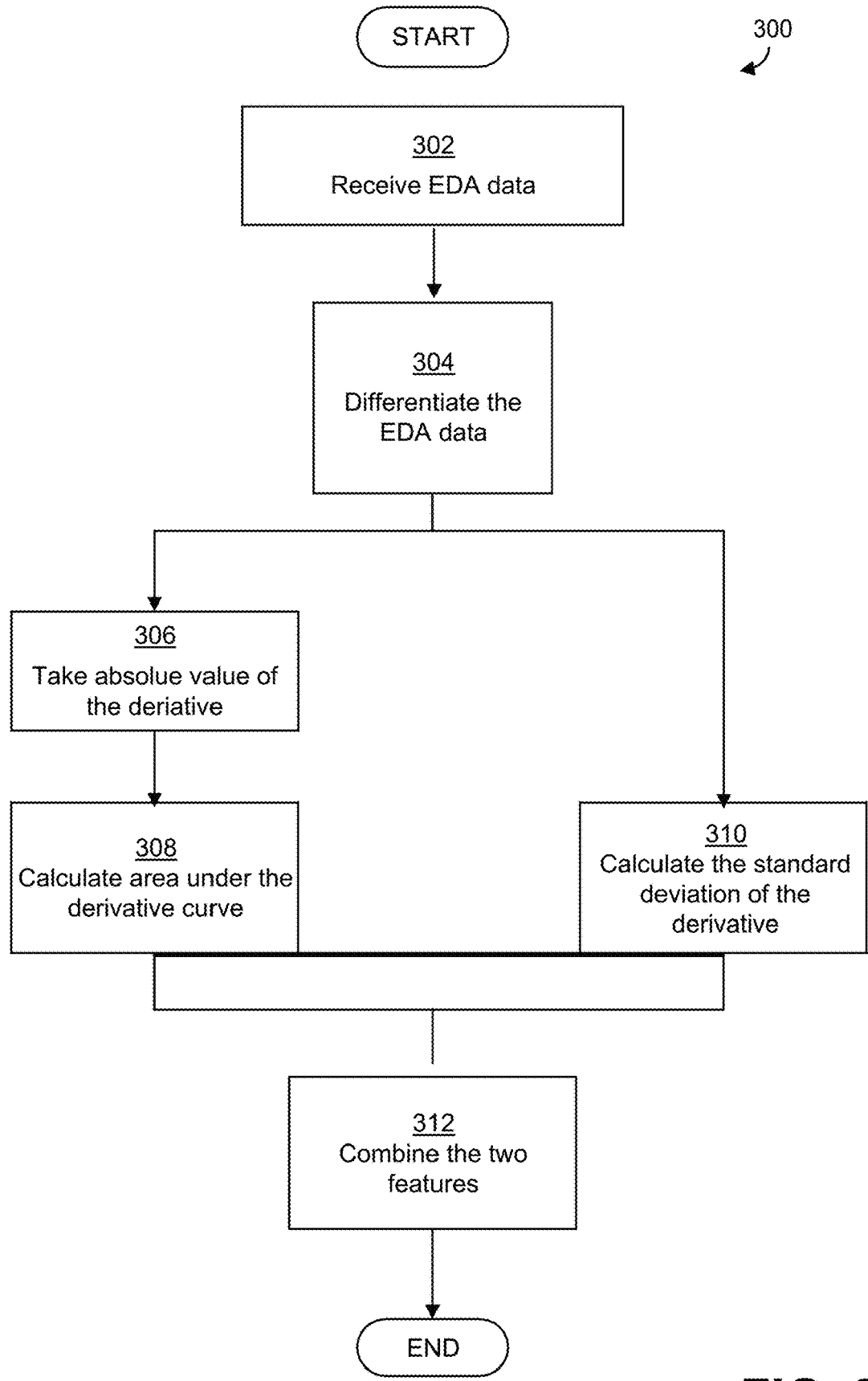
FIG. 3 is a flowchart of an example method for processing an electrodermal activity signal to determine an EDA feature.

FIG. 3 illustrates a method 300 for processing an EDA signal to obtain an EDA feature. At block 302, the seizure detection facility receives EDA data. The EDA data may be the EDA signal from the EDA sensor or a preprocessed version of the EDA signal. At act 304, the seizure detection facility differentiates the EDA data. Then, two different sub-features are calculated. At block 306, the seizure detection facility takes the absolute value of the derivative. At block 308, the seizure detection facility calculates the area under the curve of the derivative determined in block 306. This is the first sub-feature of the EDA data, and is a time-domain feature. At block 310, the seizure detection facility calculates a standard deviation of the derivative from block 304. This is the second sub-feature of the EDA data, and is also a time-domain feature. At act 312, the two sub-features are combined to form a combined EDA feature, which may be referred to as first information regarding an electrodermal activity. In some embodiments, combining the sub-features may include multiplying the two sub-features together.

Figure 4:
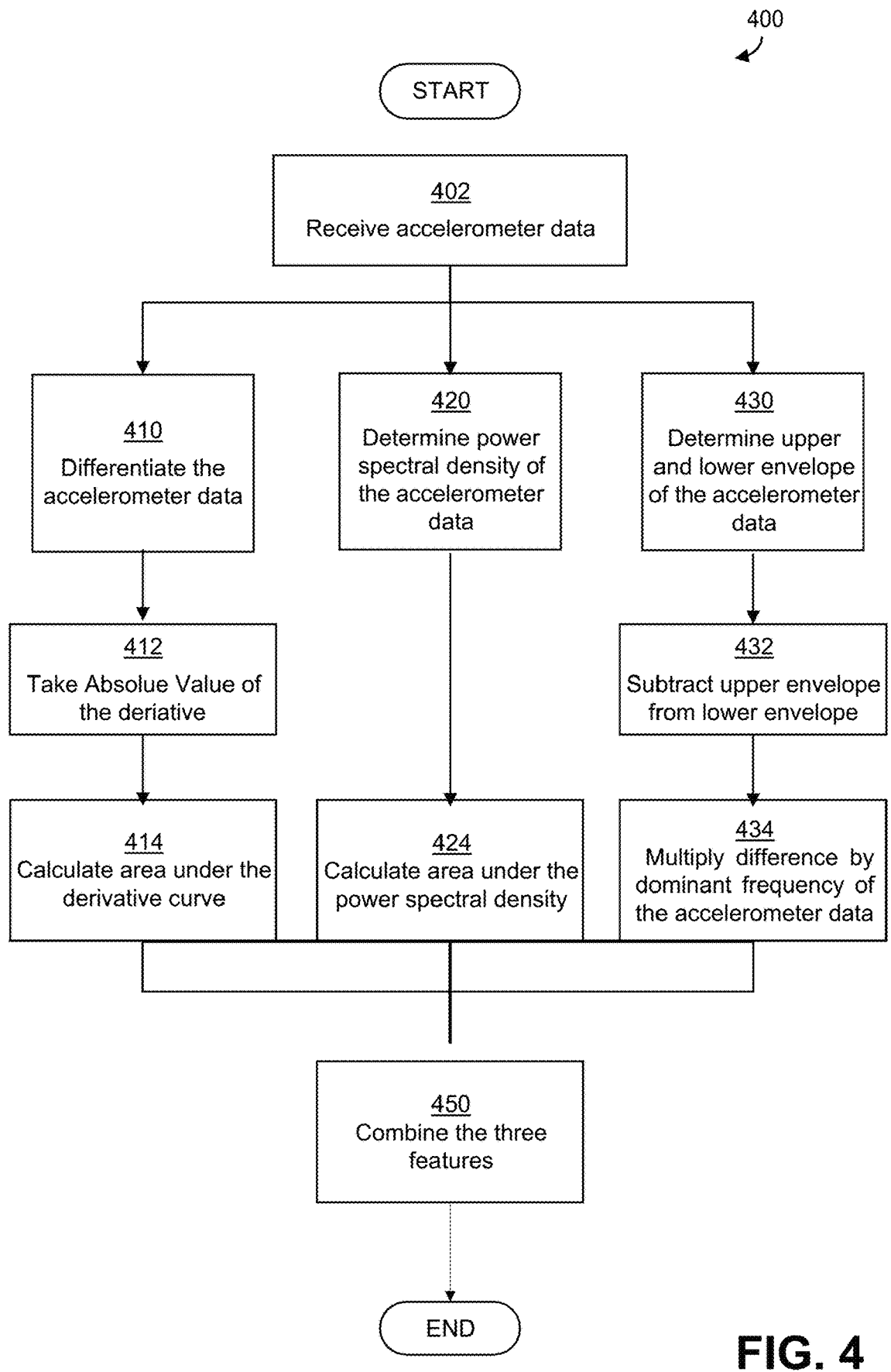
FIG. 4 is flowchart of an example method for processing an accelerometer signal to determine a motion feature.

FIG. 4 illustrates a method 400 for processing an accelerometer signal to obtain a movement feature. At block 402, the seizure detection facility receives accelerometer data. The accelerometer data may be the accelerometer signal from the accelerometer or a preprocessed version of the accelerometer signal. Three sub-features are calculated in method 400. At act 410, the seizure detection facility differentiates the accelerometer data. At block 412, the seizure detection facility takes the absolute value of the derivative. At block 414, the seizure detection facility calculates the area under the curve of the derivative determined in block 412. This is the first sub-feature of the accelerometer data, and is a time-domain feature. At block 420, the seizure detection facility determines a power spectral density of the accelerometer data. At block 424, the seizure detection facility calculates an area under the curve of the power spectral density from block 420. This is the second sub-feature of the accelerometer data, and is a frequency-domain feature. At act 430, the seizure detection facility determines an upper and lower envelope of the accelerometer data. At block 430, the seizure detection facility determines an upper and lower envelope of the accelerometer data. At block 432, the seizure detection facility subtracts the upper envelope from the lower envelope of the accelerometer data. At block 434, the seizure detection facility multiplies the difference from block 432 by a dominant frequency of the accelerometer data. The dominant frequency may be obtained from the power spectral density determines in block 420. The output of block 434 is the third sub-feature of the accelerometer data and is a combination of a time-domain feature and a frequency-domain feature. At block 450, the three sub-features are combined to form a combined accelerometer feature, which may be referred to as second information on a movement of a limb of the patient. In some embodiments, combining the sub-features may include multiplying the three sub-features together.

Figure 5:
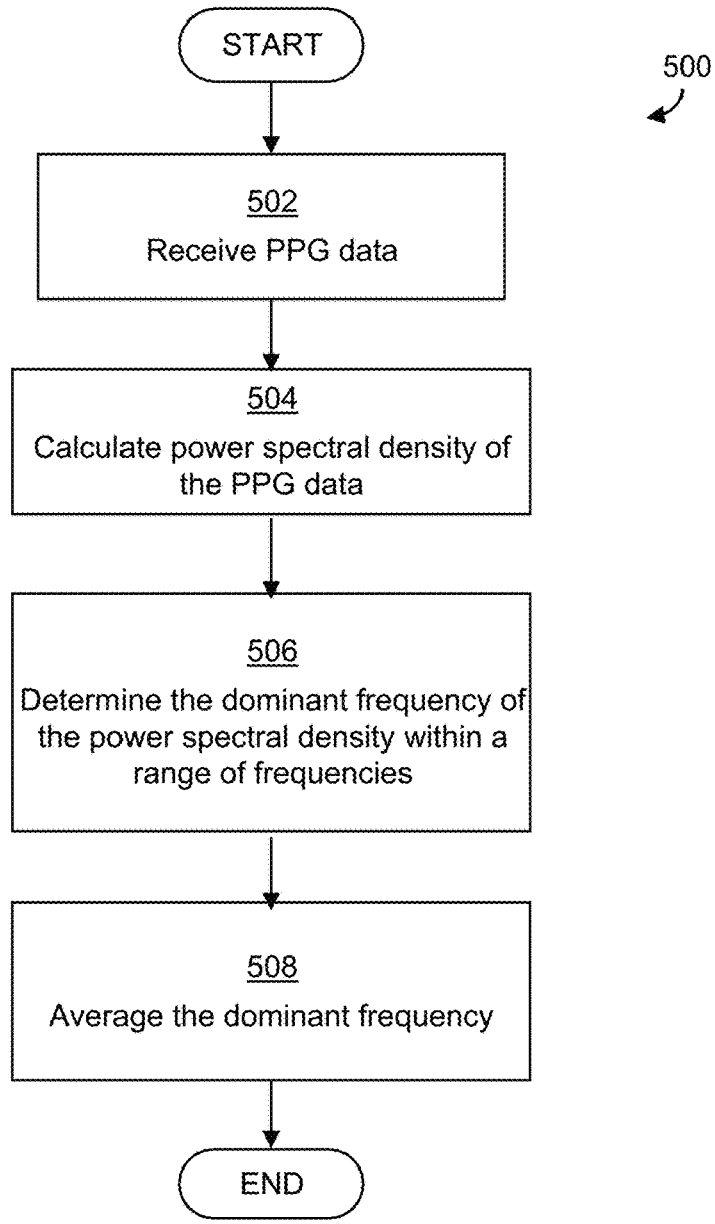
FIG. 5 is a flowchart of an example method for processing a photoplethysmogram (PPG) signal to determine a PPG feature.

FIG. 5 illustrates a method 500 of processing PPG data to obtain a PPG feature. At block 502, the seizure detection facility receives the PPG data. The PPG data may be the PPG signal from the PPG sensor or a preprocessed version of the PPG signal. At act 504, the seizure detection facility calculates a power spectral density of the PPG data. At block 506, the seizure detection facility determines a dominant frequency of the power spectral density from block 504. In some embodiments, the seizure detection facility limits the dominant frequency to be within a particular range of frequencies. For example, the dominant frequency may be the dominant frequency within the inclusive frequency range from 0.5 Hz to 3 Hz. At block 508, the seizure detection facility averages the dominant frequency from block 506. In some embodiments, the average may be a moving average. For example, a 60 second moving average window may be used. The average dominant frequency from block 508 is the PPG feature, and is a frequency-domain feature.

Returning to FIG. 2, the method 200 continues at block 210 where the seizure detection facility compares the at least one feature to a respective condition to generate a comparison result. In some embodiments, comparing a feature to a condition includes determining whether the feature is indicative of a seizure.

For example, to determine if the combined EDA feature meets an EDA condition, the seizure detection facility may subtract a reference value from the combined EDA feature and determine if the difference exceeds a threshold. In some embodiments, the reference value is a value of the combined EDA feature calculated during a resting period of the patient while not experiencing a seizure. In some embodiments, a separate awake and sleep reference value can be used. In some embodiments, the threshold may be 0.20, 0.25 or 0.30. If the current combined EDA feature exceeds the reference value by the threshold amount, then the EDA feature is said to be indicative of a seizure. The EDA comparison result may be a binary value (e.g., a Boolean value) that indicates whether the EDA condition is met. To determine if the combined accelerometer feature meets a movement condition, the seizure detection facility may determine if the combined accelerometer feature exceeds a threshold. In some embodiments, the threshold is a constant that depends on the type of accelerometer used. If the current combined accelerometer feature exceeds the threshold amount, then the accelerometer feature is said to be indicative of a seizure. The accelerometer comparison result may be a binary value (e.g., a Boolean value) that indicates whether the movement condition is met.

To determine if the PPG feature meets a PPG condition, the seizure detection facility may subtract a reference value from the PPG feature and determine if the difference exceeds a threshold. In some embodiments, the reference value is a value of the PPG feature calculated during a resting period of the patient while not experiencing a seizure (e.g., the resting heart rate of the patient). In some embodiments, a separate awake and sleep reference value can be used. In some embodiments, the threshold may be 10 beats per minute (bpm), 15 bpm, 20 bpm, or 25 bpm. If the current PPG feature exceeds the reference value by the threshold amount, then the PPG feature is said to be indicative of a seizure. The PPG comparison result may be a binary value (e.g., a Boolean value) that indicates whether the PPG condition is met.

By way of example and not limitation, the following pseudocode illustrates one possible way of implementing blocks 208 and 210 of method 200, including a preprocessing action that may take place in block 204.

| Part I-Calculating Feature from Accelerometer |
|---|
| Start by reading accelerometer data every 12 sec with 6 sec overlap with previous window<br>Step 1. Preprocessing<br>  1.1-Apply a bandpass filter with cut-off frequencies of 0.5 and 30 Hz.<br>Step 2-Calculate Sub-Feature (1): ACC_AUC based on the following steps<br>  2.1-Take the derivative of preprocessed accelerometer data<br>  2.2-Take the absolute value of the results from step 2.1.<br>  2.3-Calculate the area under the curve obtained from step 2.2.<br>Step 3-Calculate Sub-Feature (2): ACC_FFT based on the following steps<br>  3.1-Calculate power spectral density of the preprocessed accelerometer data<br>  3.2-Calculate area under the curve obtained from step 3.1.<br>Step 4-Calculate Sub-Feature (3): ACC_DEN based on the following steps |

-continued 4.1-Calculate the upper and lower envelope of the preprocessed accelerometer data
4.2-Subtract the upper envelope from the lower envelope obtained from step 4.1.
4.3-Multiply the result from step 4.2. by dominant frequency of the accelerometer
Step 5-Calculate the combined ACC Feature from the above three sub-features:
5.1-Combined feature = ACC_AUC x ACC_FFT x ACC_DEN
5.2-Compare the Combined feature (ACC_Comb) from step 5.1 to the ACC_THD*:
   if ACC_Comb> ACC_THD
     set ACC_Feature = 1
   else
     set ACC_Feature = 0
*(ACC_THD is constant and its value depends to type of accelerometer sensor)

Part II-Calculating Feature from PPG data

Start by reading PPG data every 12 sec with 6 sec overlap with previous window
Step 1. Preprocessing
1.1-Downsample the PPG data to half of its original sampling rate.
1.2-Apply a bandpass filter with cut-off frequencies of 0.1 and 20 Hz.
Step 2-Calculate Feature: PPG_HR based on the following steps
2.1-Calculate power spectral density (PSD) of the preprocessed PPG data
2.2-Keep PSDs in the frequency range of 0.5 and 3 Hz, and discard the other frequencies.
2.3-Find the dominant frequency from the results of step 2.2 and set that to heart rate (HR).
2.4-Apply a 60-sec moving average on the HR values computed from step 2.3.
2.5-Compare the average HR (HR_avg) from step 2.4 to the HR_REF*:
   if (HR_avg-HR_REF)>20 bpm
     set PPG_Feature = 1
   else
     set PPG_Feature = 0
*( HR_REF is patient's average resting heart rate (different values might be used during wake or sleep states))

Part III-Calculating Feature from EDA data

Start by reading EDA data every 1 min with 10 sec overlap with previous window
Step 1. Preprocessing
1.1-Apply a lowpass filter with cut-off frequency of 2 mHz.
1.2-Apply a Hodrick-Prescott filter with a very large smoothing factor.
Step 2-Calculate Sub-Feature (1): EDA_AUC based on the following steps
2.1-Take the derivative of preprocessed EDA data
2.2-Take the absolute value of the results from step 2.1.
2.3-Calculate the area under the curve obtained from step 2.2.
Step 3-Calculate Sub-Feature (1): EDA_STD based on the following steps
3.1-Take the derivative of preprocessed EDA data
3.2-Calculate the standard deviation of the results from 3.1.
Step 4-Calculate the combined EDA Feature from the above two sub-features:
4.1-Combined feature = EDA_AUC x EDA_STD
4.2-Compare the combined feature (EDA_Comb) from step 4.1 to the EDA_REF*:
   if (FDA Comb -EDA_REF)>0.25
     set EDA_Feature = 1
   else
     set EDA_Feature = 0
*(EDA_REF is patient's average resting EDA_Comb (different values might be used during wake or sleep states))

Figure 7:
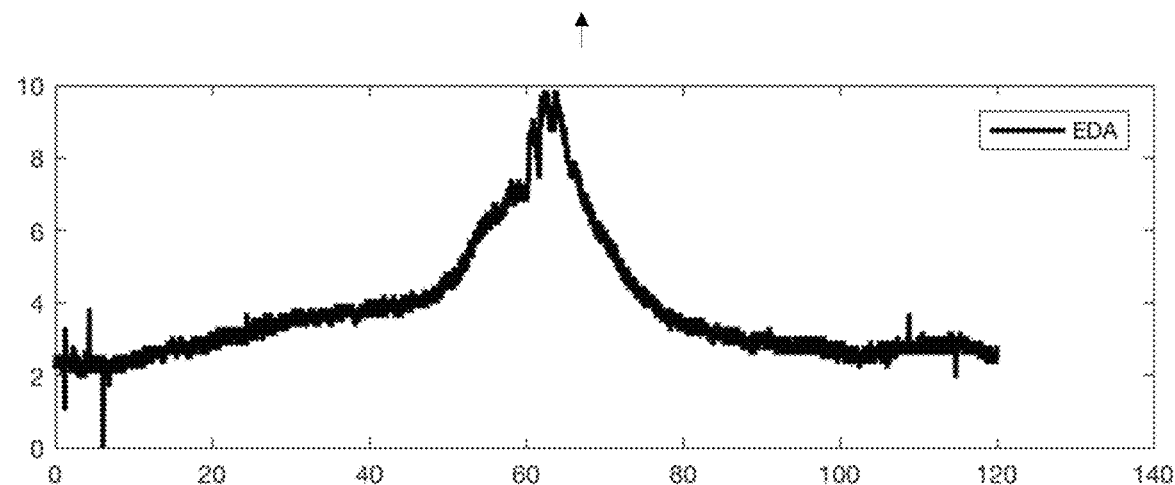
FIG. 7 includes plots of the changes of various features extracted from a blood volume signal during seizure-free periods, post-seizure periods, and pre-seizure periods.
Figure 7:
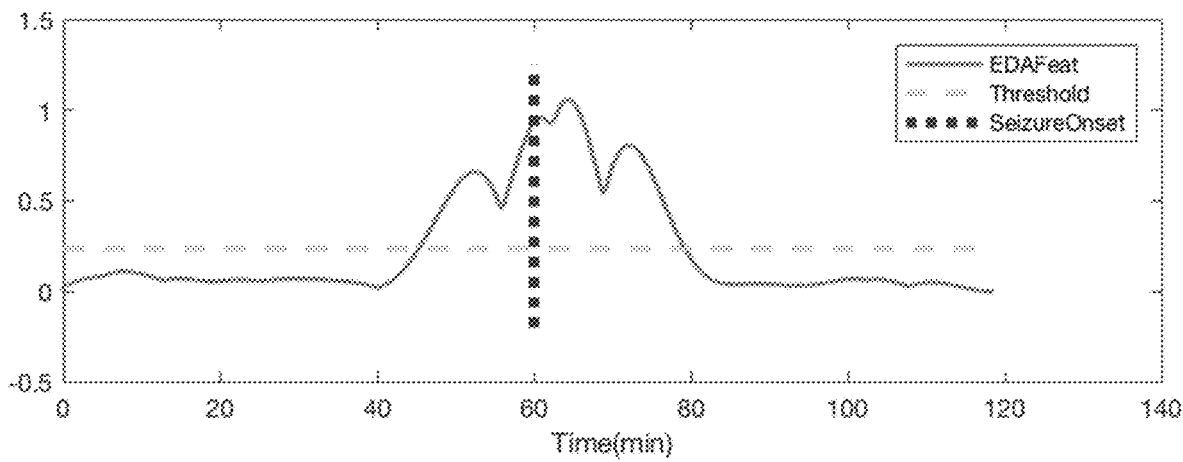
Figure 8:
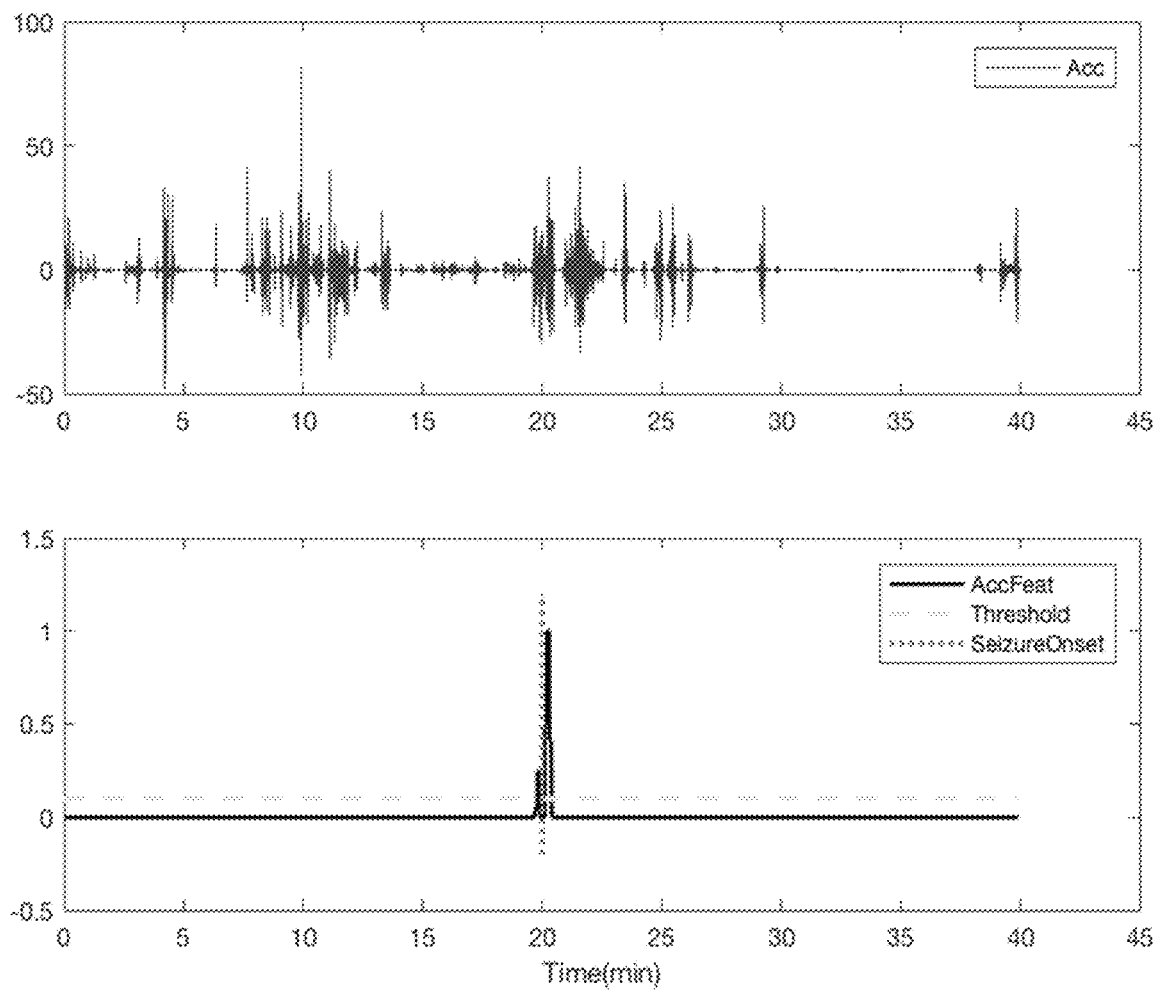
FIG. 8 includes plots of the changing pattern of various features extracted from a blood volume signal during seizure-free periods, post-seizure periods, and pre-seizure periods.
Figure 9:
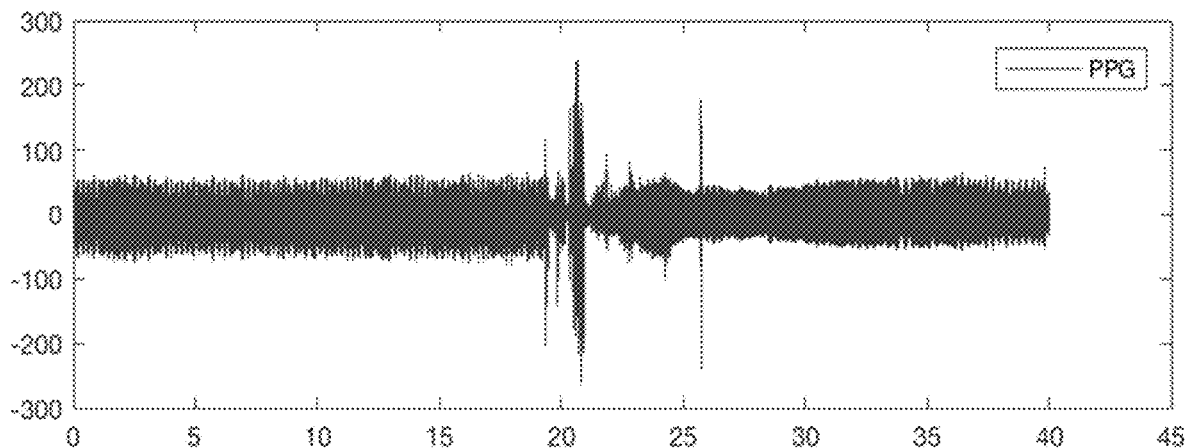
FIG. 9 includes plots of the changing pattern of the PPG feature signal during seizure-free periods, post-seizure periods, and pre-seizure periods.
Figure 9:
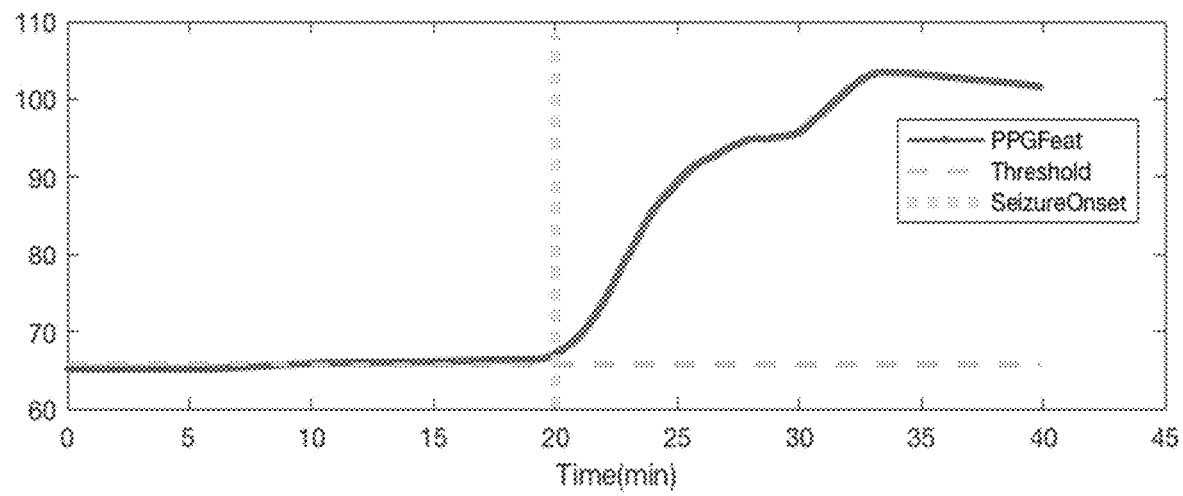

FIG. 7, FIG. 8, and FIG. 9 illustrate examples of raw EDA data, accelerometer data, and PPG data, respectively, along with each of their respective features used as an indication of a seizure. The vertical dotted line of each of FIGS. 7-9, represents the actual time of seizure onset for the patient. The horizontal dashed line of each of FIGS. 7-9 represents the threshold value for the patient. As can be seen from FIGS. 7-9, each of the respective features is more clearly correlated with the seizure onset than the associated raw data. Accordingly, these features are good indicators of a seizure.

Returning to FIG. 2, at block 212 the seizure detection facility determines a likelihood of a seizure based on the comparison results from block 210. In some embodiments, the likelihood of seizure onset determined in block 212 is based on the EDA data and the accelerometer (ACC) data, but not the PPG data. In such embodiments, there are four possible likelihoods depending on the binary values of the EDA and PPG comparison results. The following table summarizes the assigned likelihoods as a function of the binary value of the comparison results, where "1" indicates that the comparison result is indicative of a seizure and "0" indicates that the comparison result is not indicative of a seizure.

TABLE 1

Likelihood of Block 212

| ACC Comparison Result | EDA Comparison Result | First Likelihood |
| --- | --- | --- |
| 0 | 0 | 0% |
| 0 | 1 | 30% |
| 1 | 0 | 60% |
| 1 | 1 | 95% |

As is summarized by the above table, if neither the ACC nor the EDA comparison result is indicative of a seizure, the likelihood is determined to be 0%. In some embodiments, the likelihood need not be zero, but may be a value less than or equal to 10%. If both the ACC and the EDA comparison results are indicative of a seizure, the likelihood is determined to be 95%. In some embodiments, the likelihood need not be 95%, but may be a value greater than or equal to 90%. If the ACC comparison result is indicative of a seizure but the EDA comparison result is not, the likelihood is determined to be 60%. In some to embodiments, the likelihood need not be 60%, but may be a value greater than or equal to 50% and less than or equal to 70%. If the ACC comparison result is not indicative of a seizure but the EDA comparison result is, the likelihood is determined to be 30%. In some embodiments, the likelihood need not be 30%, but may be a value greater than or equal to 25% and less than or equal to 40%.

At block 214, the seizure detection facility triggers a presentation of an alert when the first likelihood satisfies a first detection criterion. The detection criterion can be determined based on the particular patient or a caregiver to the patient. In some embodiments, the detection criterion may be the likelihood exceeding a threshold. In other embodiments, the detection criterion may be the likelihood continuously exceeding a threshold for a threshold period of time. In some embodiments, the notification may be an alert displayed on a display or a sound delivered by a speaker. In some embodiments, the alert may include presenting the likelihood to the patient or a caregiver of the patient. Accordingly, the alert may be output for display on the device 104, device 106, and/or device 114 of FIG. 1.

The method 200 continues to block 216, where the seizure detection facility determines whether the second time interval expired. If not, then the method 200 returns to block 202. If the second time interval is determined to have expired, the method continues to block 218. Using a longer second time interval allows the PPG data, which is not been conventionally used in detecting a seizure due to the aforementioned difficulty in accurately determining heart rate during a seizure, to be used in seizure detection. As shown in FIG. 9, the PPG feature extracted from the PPG data (e.g., a moving average of the patient's heart rate) increases significantly after the onset of a seizure. Accordingly, the PPG data can be used to increase the likelihood of a seizure event having occurred relative to seizure events determined during the shorter first time interval based on the movement feature and EDA feature.

At block 218, the seizure detection facility determines at least one feature from at least one of the plurality of biomedical signals. The feature determination here may include any of the features discussed in connection with block 208 of method 200.

At block 220, the seizure detection facility determines whether at least one feature meets a detection criterion. In some embodiments, the at least one feature is a PPG feature determined from the PPG data and the criterion in a PPG criterion. For example, if the PPG feature exceeds a base value by a threshold amount, as described above, then the detection criterion is determined to be met. If the detection criterion is not met, then the likelihood, as determined in block 212 is maintained as the current seizure likelihood. If the detection criterion is met at block 220, then the method 200 continues to block 222 and block 224, where features from block 218 are compared to respective conditions and a second likelihood is determined based on the comparison results in a similar way as discussed in connection with locks 210 and 212.

While the example of block 218, 220, 222 described above includes generation of new features and new comparisons to conditions, embodiments are not so limited. In some embodiments, each of the features may be newly determined upon expiration of the second time interval. In other embodiments, one or more of the features or comparison results may have been previously determined, such as in response to a prior expiration of the first time interval, and may have been stored in storage for later retrieval in response to expiration of the second time interval. Upon expiration of the second time interval, for example, a query may be made for one or more features that were determined in a time period (e.g., five minutes, seven minutes, ten minutes, the length of the second time interval, etc.) prior to expiration of the second time interval, and the retrieved feature(s) or comparison results may be used in determining the second likelihood.

As a particular example of such an approach, a query may be made upon expiration of a second time interval for any comparison results since the last expiration of the second time interval that indicated that an EDA condition or a movement condition was met. Such indications of EDA and/or movement conditions being met are indicative of a potential seizure since the prior expiration of the second time interval. These values may be used together with a new PPG signal analysis and comparison result to determine a likelihood that a patient experienced a seizure during the second time interval.

At block 224 the seizure detection facility determines a second likelihood of a seizure based on the comparison results from block 222. In some embodiments, the likelihood of seizure onset determined in block 224 is based on the EDA data and the accelerometer (ACC) data and the PPG data. If the PPG comparison result does not indicate a seizure, a second likelihood is not calculated and the method 200 returns to block 202, as discussed in connection with block 220. Thus, the current likelihood is maintained at whatever likelihood was determined in block 212. If the PPG data does indicate a seizure, there are four possible likelihoods depending on the binary values of the EDA and PPG comparison results. The following table summarizes the assigned likelihoods as a function of the binary value of the comparison results, where "1" indicates that the comparison result is indicative of a seizure and "0" indicates that the comparison result is not indicative of a seizure.

TABLE 2

| Likelihood of Block 222 | | |
| --- | --- | --- |
| ACC Comparison Result | EDA Comparison Result | Second Likelihood |
| 0 | 0 | $1^{st}$ Likelihood |
| 0 | 1 | 65% |
| 1 | 0 | 95% |
| 1 | 1 | 100% |

As is summarized by the above table, if neither the ACC nor the EDA comparison result is indicative of a seizure, the likelihood is maintained the same as the first likelihood determined in block 212. If both the ACC and the EDA comparison results are indicative of a seizure, the likelihood is determined to be 100%. If the ACC comparison result is indicative of a seizure but the EDA comparison result is not, the likelihood is determined to be 95%. In some embodiments, the likelihood need not be 95%, but may be a value greater than or equal to 80% and less than or equal to 100%. If the ACC comparison result is not indicative of a seizure but the EDA comparison result is, the likelihood is determined to be 65%. In some embodiments, the likelihood need not be 65%, but may be a value is greater than or equal to 50% and less than or equal to 80%.

By way of example and not limitation, the following pseudocode illustrates one possible way of implementing blocks 212 and 224 of method 200, assuming all the features and comparison results are known.

```
Part IV - Seizure Detection Strategy based on the above calculated features

Step 1 - Every 60^sec check
(1) if EDA_feature alone showed a period of status change (EDA_feature =1)
    { (2) if ACC_feature also showed a period of status change (ACC_feature = 1)
              { set GTC_probability = 95%
              else
                  set GTC_probability = 30%
    } // end if (2)
  else
    { (3) if ACC_feature only showed a period of status change (ACC_feature = 1)
              { set GTC_probability = 60%
              else
                  set GTC_probability = 0%
```

Part IV - Seizure Detection Strategy based on the above calculated features

```
            } // end if (3)
    } // end if(1)
Step 2 - Every 10-min check
(1) if PPG_feature showed a period of status change (PPG_feature =1)
    { (2) if both ACC_feature and EDA_feature were 1 in a limited time interval
        { set GTC_probability = 100% } // end if (2)
        (3) else if only ACC_feature was 1 in a limited time interval but EDA_feature=0
        { set GTC_probability = 95% } // end if (3)
        (4) else if only EDA_feature was 1 in a limited time interval but ACC_feature=0
        { set GTC_probability = 65%} // end if (4)
    else
                Do not change GTC_probability
        } // end if (1)
```

Returning to FIG. 2, at block 226 the seizure detection facility triggers presentation of an alert when the second likelihood satisfies a second detection criterion. The second detection criterion can be determined based on the particular patient or a caregiver to the patient. In some embodiments, the detection criterion may be the likelihood exceeding a threshold. In other embodiments, the detection criterion may be the likelihood continuously exceeding a threshold for a threshold period of time. In some embodiments, the notification may be an alert displayed on a display or a sound delivered by a speaker. In some embodiments, the alert may include presenting the likelihood to the patient or a caregiver of the patient. Accordingly, the alert may be output for display on the device 104, device 106, and/or device 114 of FIG. 1.

After block 226 is complete, the method 200 returns back to block 202 and continues the loop of the method 200 until the method is interrupted or otherwise instructed to end.

While the example of FIG. 2 includes monitoring the signals in block 202, outside of the context of the time intervals of FIG. 2, it should be appreciated that embodiments are not so limited. In some embodiments, in response to expiration of the first and/or second time intervals, data may be collected from one or more sensors (and, in some embodiments, pre-processed) and then processed to generate one or more features. Accordingly, in such an embodiment, the biomedical signals may not be continuously monitored, but may only be monitored upon expiration of the first and/or second time intervals.

Computer-Implemented Embodiments

Techniques operating according to the principles described herein may be implemented in any suitable manner. Included in the discussion above are a series of flow charts showing the steps and acts of various processes that detect the occurrence of a seizure based on analysis of multiple biomedical signals. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein. Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some example functional facilities have been described herein for carrying out one or more tasks. It should be appreciated, though, that the functional facilities and division of tasks described is merely illustrative of the type of functional facilities that may implement the example techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 612 of FIG. 6 described below (i.e., as a portion of a computing device 600) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the example computer system of FIG. 1, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 6:
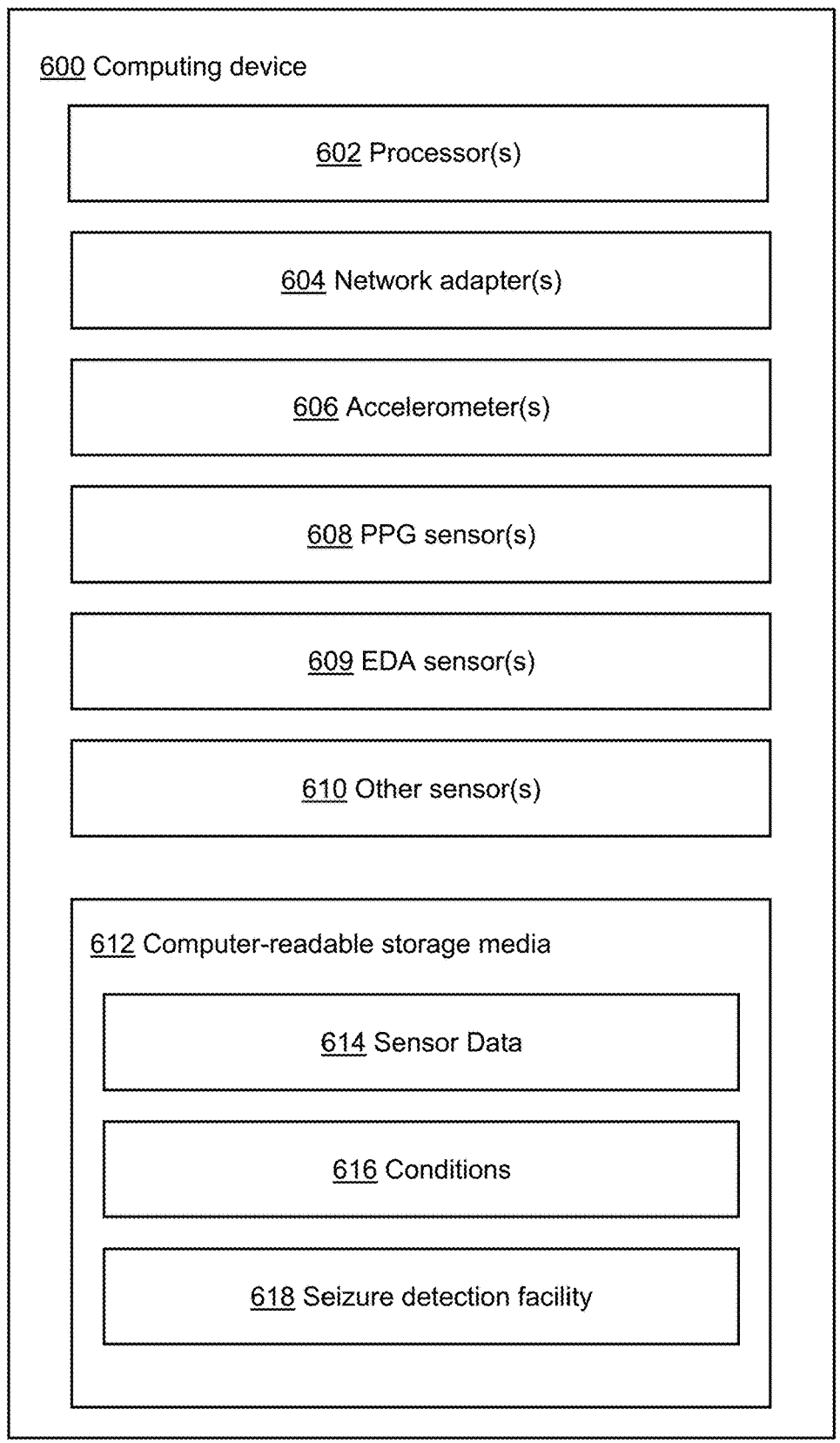
FIG. 6 is a block diagram of an example of a computing device with which some embodiments may operate.

FIG. 6 illustrates one example implementation of a computing device in the form of a computing device 600 that may be used in a system implementing techniques described herein, although others are possible. Computing device 600 may, for example, be implemented as a wearable device, such as device 104 of FIG. 1. It should be appreciated that FIG. 6 is intended neither to be a depiction of necessary components for a computing device to operate as a wearable device 104 or any other computing device of a system operating according to techniques described herein, nor a comprehensive depiction.

Computing device 600 may comprise at least one processor 602, a network adapter 604, and computer-readable storage media 612. Computing device 600 may be, for example, a wearable device, a desktop or laptop personal computer, a personal digital assistant (PDA), a smart mobile phone, a tablet computer, a server, or any other suitable computing device. Network adapter 604 may be any suitable hardware and/or software to enable the computing device 600 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 612 may be adapted to store data to be processed and/or instructions to be executed by processor 602. Processor 602 enables processing of data and execution of instructions. The data and instructions may be stored on the computer-readable storage media 612 and may, for example, enable communication between components of the computing device 600.

Device 600 may, in some embodiments (e.g., embodiments in which the device 600 is a wearable device), include one or more sensors to measure biomedical characteristics or other data associated with a patient. In the example of FIG. 6, the device 600 includes one or more accelerometers 606, one or more PPG sensors 608, one or more EDA sensors 609, and one or more other sensors 610, which may include, for example, a thermometer or an electrocardiogram (EKG) sensor.

The data and instructions stored on computer-readable storage media 612 may comprise computer-executable instructions implementing techniques which operate according to the principles described herein. In the example of FIG. 6, computer-readable storage media 612 stores computer-executable instructions implementing various facilities and storing various information as described above. Computer-readable storage media 612 may store sensor data 614, such as PPG signal data, acceleration data, EDA data, or other data from the other sensors 610. The media 612 may further store data 616 on conditions such as baseline values (e.g., values of features while the patient is not experiencing a seizure) and threshold values. The media 612 may additionally store instructions for a seizure detection facility 618, which may implement any of the techniques described above for predicting occurrence of a seizure during a time period.

While not illustrated in FIG. 6, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Experimental Results

An embodiment of the above-described technique was tested 12,000 batches of data from each of 30 patients. The following performance table indicates that the above ACC, EDA and PPG features are highly sensitive and reliable at detecting seizures.

TABLE 3

Performance Table (Where "ACC only" indicates basing seizure detection on accelerometer data alone; "ACC + EDA" indicates basing seizure detection on accelerometer data and EDA data; and "ACC + EDA + HR" indicates basing seizure detection on accelerometer data, EDA data, and PPG heart rate (HR) data.

|  | ACC only | ACC + EDA | ACC + EDA + HR |
| --- | --- | --- | --- |
| Specificity | 100% | 100% | 100% |
| Sensitivity | 96.6% | 100% | 100% |

Additional Considerations

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

The invention claimed is:

1. A method comprising:
   receiving, by a processor of a patient device, biometric data of a patient, the biometric data comprising:
      a first information associated with measurement, by a sensor of the patient device, of electrodermal activity of the patient,
      a second information associated with measurement, by the sensor of the patient device, of movement of a limb of the patient,
      a third information associated with measurement, by a photoplethysmogram (PPG) sensor of the patient device, of heart rate of the patient,
   upon expiration of a first time interval, determining, by the processor, whether the patient is experiencing a seizure, wherein determining whether the patient is experiencing the seizure comprises:
      comparing the first information regarding the electrodermal activity of the patient to at least one first condition to generate a first comparison result;
      comparing the second information on the movement of a limb of the patient to at least one second condition to generate a second comparison result;
      generating a first likelihood based at least in part on the first comparison result and the second comparison result;
      in response to determining that the first likelihood satisfies at least a first detection criterion, triggering presentation of a first alert regarding a potential seizure; and
   upon expiration of a second time interval longer than the first time interval, determining, by the processor, whether the patient experienced a seizure in the second time interval, the determining whether the patient experienced a seizure comprising:
      processing the third information regarding the heart rate of the patient to generate power spectral density (PSD) of the heart rate during the second time interval;
      determining the heart rate to be a PSD-based heart rate of at least one portion of the second time interval based at least in part on a dominant frequency of the PSD during the at least one portion of the second time interval;
      comparing the PSD-based heart rate to at least one reference heart rate to generate a third comparison result;
      generating a second likelihood based at least in part on the third comparison result and the first likelihood;
      in response to determining that the second likelihood satisfies at least a third detection criterion:
         triggering presentation of a second alert regarding a potential seizure.

2. The method of claim 1, wherein the first alert comprises an indication of the first likelihood and the second alert comprises an indication of the second likelihood.

3. The method of claim 2, wherein each of the first, second, and third comparison result is a binary value.

4. The method of claim 3, wherein generating the first likelihood comprises selecting a value from four predetermined values based on the binary values of the first and second comparison result.

5. The method of claim 4, wherein selecting the value from the four predetermined values comprises:
selecting a first value of the four values when the first comparison result indicates that the first information met the at least one first condition and the second comparison result indicates that the second information met the at least one second condition;
selecting a second value of the four values when the first comparison result indicates that the first information met the at least one first condition and the second comparison result indicates that the second information did not meet the at least one second condition;
selecting a third value of the four values when the first comparison result indicates that the first information did not meet the at least one first condition and the second comparison result indicates that the second information met the at least one second condition;
selecting a fourth value of the four values when the first comparison result indicates that the first information did not meet the at least one first condition and the second comparison result indicates that the second information did not meet the at least one second condition, wherein:
the first value is greater than the third value,
the third value is greater than the second value, and
the second value is greater than the fourth value.

6. The method of claim 5, wherein:
the first value is greater than or equal to 90%;
the second value is greater than or equal to 25% and less than or equal to 40%;
the third value is greater than or equal to 50% and less than or equal to 70%; and
the fourth value is less than or equal to 10%.

7. The method of claim 3, wherein generating the second likelihood comprises selecting a value from four predetermined values based on the binary values of the first, second, and third comparison result.

8. The method of claim 7, wherein selecting the value from the four predetermined values comprises:
selecting a first value of the four values when a fourth comparison result indicates that a fourth information met the at least one first condition and a fifth comparison result indicates that a fifth information met the at least one second condition;
selecting a second value of the four values when the fourth comparison result indicates that the fourth information met the at least one first condition and the fifth comparison result indicates that the fifth information did not meet the at least one second condition;
selecting a third value of the four values when the fourth comparison result indicates that the fourth information did not meet the at least one first condition and the fifth comparison result indicates that the fifth information met the at least one second condition;
selecting a fourth value of the four values when the fourth comparison result indicates that the fourth information did not meet the at least one first condition and the fifth comparison result indicates that the fifth information did not meet the at least one second condition, wherein:
the first value is greater than the second, third and fourth value,
the third value is greater than the second value, and
the fourth value is equal to the first likelihood.

9. The method of claim 8, wherein:
the first value is equal to 100%;
the second value is greater than or equal to 60% and less than or equal to 70%; and
the third value is greater than or equal to 85% and less than or equal to 95%.

10. The method of claim 1, further comprising determining the first information based on electrodermal data.

11. The method of claim 10, further comprising filtering the electrodermal data with a lowpass filter prior to determining the first information.

12. The method of claim 1, further comprising determining the third information based on photoplethysmogram (PPG) data.

13. The method of claim 12, wherein comparing the third information to the at least one third condition comprises determining whether the third information is indicative of a seizure.

14. The method of claim 12, further comprising:
determining a heart rate of the patient based on the PPG data; and
determining the third information based on the heart rate.

15. The method of claim 14, further comprising determining the third information based on a moving average value of the heart rate.

16. The method of claim 15, further comprising determining the third information based on a difference between a reference heart rate of the patient and the moving average value of the heart rate.

17. The method of claim 16, wherein comparing the third information to the at least one third condition comprises comparing the difference between a reference heart rate of the patient and the moving average value of the heart rate to a heart rate threshold value.

18. A device comprising:
at least one processor; and
at least one storage having encoded thereon executable instructions that, when executed by the at least one processor, cause the at least one processor to perform the method of claim 1.

19. The device of claim 18, further comprising:
an electrodermal activity sensor configured to detect electrodermal activity and output electrodermal data;
an accelerometer configured to detect motion of the limb of the patient and output accelerometry data; and
a pulse oximeter configured to detect a heart rate of the patient and output photoplethysmogram (PPG) data.

20. At least one non-transitory storage medium encoded with executable instructions that, when executed by at least one processor, cause the at least one processor to carry out the method of claim 1.

* * * * *